(12) United States Patent
Freehauf et al.

(10) Patent No.: US 9,770,440 B2
(45) Date of Patent: Sep. 26, 2017

(54) SOLID ORAL PHARMACEUTICAL COMPOSITIONS FOR ISOXAZOLINE COMPOUNDS

(71) Applicant: Intervet Inc., Summit, NJ (US)

(72) Inventors: Keith Freehauf, Stockton, NJ (US); Niki Waldron, Piscataway, NJ (US); Jürgen Lutz, Wiesbaden (DE); Frank Guerino, Monroe Township, NJ (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/390,052

(22) PCT Filed: Apr. 3, 2013

(86) PCT No.: PCT/EP2013/056992
§ 371 (c)(1),
(2) Date: Oct. 2, 2014

(87) PCT Pub. No.: WO2013/150055
PCT Pub. Date: Oct. 10, 2013

(65) Prior Publication Data
US 2015/0057239 A1  Feb. 26, 2015

Related U.S. Application Data

(60) Provisional application No. 61/782,028, filed on Mar. 14, 2013.

(30) Foreign Application Priority Data

Apr. 4, 2012  (EP) ..................... 12163198

(51) Int. Cl.
| | | |
|---|---|---|
| *A61K 31/42* | (2006.01) | |
| *A01N 43/80* | (2006.01) | |
| *A61K 31/7048* | (2006.01) | |
| *A61K 31/35* | (2006.01) | |
| *A61K 31/422* | (2006.01) | |
| *A61K 47/38* | (2006.01) | |
| *A61K 47/22* | (2006.01) | |
| *A61K 47/16* | (2006.01) | |
| *A61K 45/06* | (2006.01) | |
| *A61K 9/00* | (2006.01) | |
| *A61K 47/12* | (2006.01) | |
| *B29C 37/00* | (2006.01) | |
| *A61K 47/18* | (2017.01) | |
| *A61K 9/14* | (2006.01) | |
| *A61K 9/16* | (2006.01) | |
| *A61K 9/20* | (2006.01) | |
| *A61K 9/28* | (2006.01) | |
| *A61K 9/48* | (2006.01) | |
| *A61K 9/50* | (2006.01) | |
| *A61K 9/51* | (2006.01) | |
| *B29L 31/00* | (2006.01) | |

(52) U.S. Cl.
CPC ............ *A61K 31/42* (2013.01); *A61K 9/0056* (2013.01); *A61K 9/145* (2013.01); *A61K 9/1617* (2013.01); *A61K 9/2013* (2013.01); *A61K 9/282* (2013.01); *A61K 9/4858* (2013.01); *A61K 9/5015* (2013.01); *A61K 9/5123* (2013.01); *A61K 31/35* (2013.01); *A61K 31/422* (2013.01); *A61K 31/7048* (2013.01); *A61K 45/06* (2013.01); *A61K 47/12* (2013.01); *A61K 47/16* (2013.01); *A61K 47/18* (2013.01); *A61K 47/22* (2013.01); *A61K 47/38* (2013.01); *B29C 37/0003* (2013.01); *B29L 2031/753* (2013.01)

(58) Field of Classification Search
CPC ...... A61K 31/35; A61K 31/42; A61K 31/422; A61K 31/7048; A61K 45/06; A61K 47/12; A61K 47/16; A61K 47/18; A61K 47/22; A61K 47/38; A61K 9/0056; A61K 9/145; A61K 9/1617; A61K 9/2013; A61K 9/282; A61K 9/4858; A61K 9/5015; A61K 9/5123
USPC .................................................. 514/30, 378
See application file for complete search history.

(56) References Cited

U.S. PATENT DOCUMENTS

| | | | | |
|---|---|---|---|---|
| 7,955,632 B2 * | 6/2011 | Paulsen | ................ | A61K 9/0056 424/439 |
| 8,563,474 B2 * | 10/2013 | Koerber | ................ | A01N 43/80 504/138 |
| 8,633,134 B2 * | 1/2014 | Kaiser | .................... | A01N 43/80 504/100 |
| 9,173,870 B2 * | 11/2015 | Fuchs | .................... | A61K 31/42 |
| 9,233,100 B2 * | 1/2016 | Soll | ........................ | A61K 45/06 |
| 9,259,417 B2 * | 2/2016 | Soll | ........................ | A61K 45/06 |
| 2007/0066617 A1 | 3/2007 | Mita et al. | | |

(Continued)

FOREIGN PATENT DOCUMENTS

| | | | | | |
|---|---|---|---|---|---|
| DE | WO 2012089622 A2 * | 7/2012 | ............ | A61K 31/42 |
| WO | 2005085216 A1 | 9/2005 | | |

(Continued)

OTHER PUBLICATIONS

PCT International Search Report for corresponding PCT/EP2013/056992, mailed on Jun. 10, 2013, 5 Pages.

*Primary Examiner* — My-Chau T Tran

(57) ABSTRACT

A solid oral pharmaceutical composition for delivery of a pharmaceutically acceptable active ingredient to an animal where the composition comprises an isoxazoline compound, a solvent and an excipient, a process for the manufacture of such solid oral pharmaceutical composition and a method of controlling a parasite infection administering such solid oral pharmaceutical composition.

18 Claims, 2 Drawing Sheets

(56) References Cited

U.S. PATENT DOCUMENTS

| | | | |
|---|---|---|---|
| 2010/0279999 A1 | 11/2010 | Renold et al. | |
| 2011/0118212 A1 | 5/2011 | Koerber et al. | |
| 2011/0245239 A1 | 10/2011 | Nanchen et al. | |
| 2014/0343085 A1* | 11/2014 | Desevaux | A61K 31/42 514/275 |
| 2015/0057321 A1* | 2/2015 | Alteheld | A61K 31/42 514/378 |

FOREIGN PATENT DOCUMENTS

| | | |
|---|---|---|
| WO | 2007079162 A1 | 7/2007 |
| WO | 2007095156 A2 | 8/2007 |
| WO | 2009002809 A2 | 12/2008 |
| WO | 2009003075 A1 | 12/2008 |
| WO | 2009024541 A3 | 2/2009 |
| WO | 2009064859 | 5/2009 |
| WO | 2009080250 A2 | 7/2009 |
| WO | 2010039892 | 4/2010 |
| WO | 2010070068 A2 | 6/2010 |
| WO | 2010079077 A1 | 7/2010 |
| WO | 2011075591 A1 | 6/2011 |
| WO | 2011124998 A1 | 10/2011 |

* cited by examiner

SOLID ORAL PHARMACEUTICAL COMPOSITIONS FOR ISOXAZOLINE COMPOUNDS

CROSS-REFERENCE TO RELATED APPLICATIONS

This application is a national stage entry under 35 U.S.C. §371 of PCT/EP2013/056992, filed on Apr. 3, 2013, which claims priority to U.S. Provisional Application No. 61/782,028, filed on Mar. 14, 2013, and EP Application No. 12163198.0, filed on Apr. 4, 2012. The content of PCT/EP2013/056987 is hereby incorporated by reference in its entirety.

BACKGROUND OF THE INVENTION

A number of parasites can infest or infect domestic animals especially also companion animals such as cats and dogs. These pests and parasites are of great nuisance to both the animals and their owners.

Isoxazoline compounds are known in the art and these compounds and their use as antiparasitic are described, for example, in US patent application US 2007/0066617, and International Patent applications WO 2005/085216, WO 2007/079162, WO 2009/002809, WO 2009/024541, WO 2009/003075, WO 2009/080250, WO 2010/070068 and WO 2010/079077, the disclosures of which, as well as the references cited herein, are incorporated by reference.

This class of compounds is known to possess excellent activity against ectoparasites, i.e. parasitic insect and acarids, such as ticks and fleas and endoparasites such as nematodes.

Examples of isoxazoline compounds are carbamoyl benzamide phenyl isoxazoline (CBPI) compounds. A specific example of a CBPI compound is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN [864731-61-3])—USAN fluralaner.

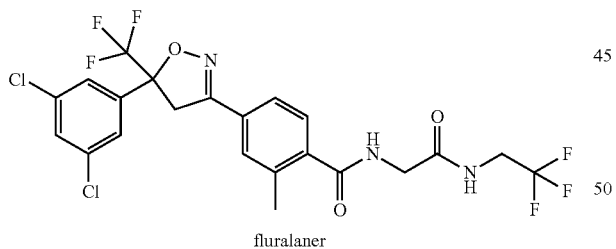

fluralaner

The CBPI compound fluralaner is disclosed in patent application WO 2005/085216.

As these isoxazoline compounds have been originally investigated for their use in the agricultural area it is necessary to identify specific formulations that allow their veterinary use, i.e. safe administration to control parasites in animals effectively.

One known and convenient way of administering an ectoparasiticide compound to an animal is oral administration, e.g. as solid oral formulation such as tablets or soft chews that have a high bioavailability to allow the control of parasites with a low dosage of the ectoparasiticide compound orally administered to the animal.

SUMMARY OF THE INVENTION

In one aspect the current invention is directed to a solid oral pharmaceutical composition comprising an effective amount of at least one isoxazoline compound of the Formula (I)

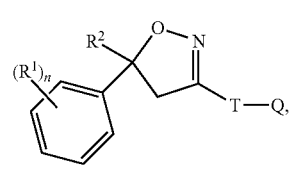

Formula (I)

wherein $R^1$=halogen, $CF_3$, $OCF_3$, CN, n=integer from 0 to 3, preferably 1, 2 or 3, $R^2$=$C_1$-$C_3$-haloalkyl, preferably $CF_3$ or $CF_2Cl$, T=5- or 6-membered ring, which is optionally substituted by one or more radicals Y, Y=methyl, halomethyl, halogen, CN, $NO_2$, $NH_2$—C=S, or two adjacent radicals Y form together a chain, especially a three or four membered chain;

Q=X—$NR^3R^4$ or a 5-membered N-heteroaryl ring, which is optionally substituted by one or more radicals;

X=$CH_2$, $CH(CH_3)$, CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

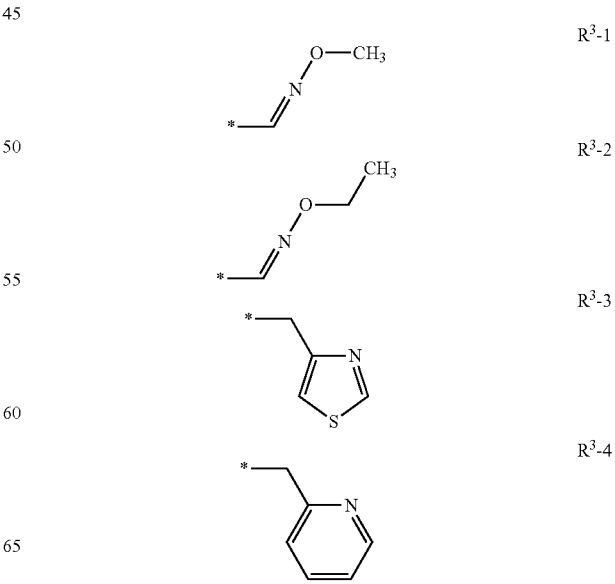

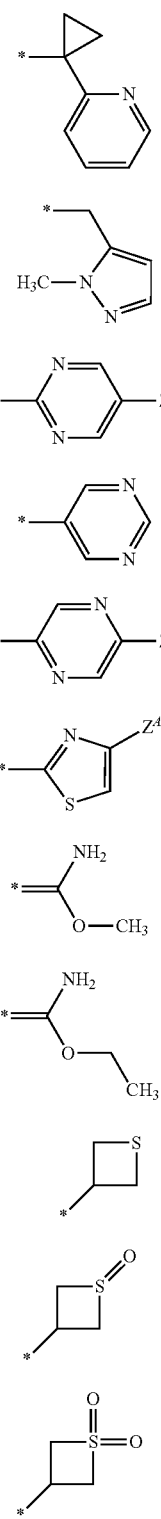

wherein $Z^A$=hydrogen, halogen, cyano, halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

or $R^3$ and $R^4$ together form a substituent selected from the group consisting of:

or a salt or solvate thereof, a solid carrier and a solvent, wherein the solvent is selected from 2-pyrrolidone, dimethylacetamide or mixtures thereof.

In a preferred embodiment the solid oral pharmaceutical composition is a soft chewable veterinary pharmaceutical composition for oral administration.

In a preferred embodiment the solid carrier is microcrystalline cellulose.

In one embodiment the composition further comprises pamoic acid or a pharmaceutically acceptable salt thereof.

In one embodiment the isoxazoline compound is fluralaner.

In one embodiment the isoxazoline compound is 4-[5-(3,5-dichlorophenyl)-4,5-dihydro-5-(trifluoromethyl)-3-isoxazolyl]-N—[(Z)-(methoxyimino)methyl]-2-methylbenzamide.

In one embodiment the isoxazoline compound is afoxolaner.

In one embodiment the isoxazoline compound is 4-[5-(3,5-dichlorophenyl)-5-(trifluoromethyl)-4H-isoxazol-3-yl]-2-methyl-N-(thietan-3-yl)benzamide.

In one embodiment the isoxazoline compound is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino] ethyl]-2-thiophenecarboxamide.

In one embodiment the solid oral pharmaceutical composition comprises an additional pharmaceutically active compound.

In one embodiment the additional pharmaceutically active compound is a macrocyclic lactone selected from the group of ivermectin, milbemycin, and moxidectin.

In one embodiment the solid oral pharmaceutical composition comprises an isoxazoline compound of Formula (I) or a salt or solvate thereof, 2-pyrrolidone, microcrystalline cellulose, sodium starch glycolate, sodium lauryl sulfate, sodium pamoate, magnesium stearate, aspartame, glycerol, soybean oil, and polyethylene glycol In another embodiment the solid oral pharmaceutical composition comprises an isoxazoline compound of Formula (I) or a salt or solvate thereof, dimethyl acetamide, microcrystalline cellulose, sodium starch glycolate, sodium lauryl sulfate, sodium pamoate, magnesium stearate, aspartame, glycerol, soybean oil, and polyethylene glycol.

Another aspect of the invention is a method of preparing a solid pharmaceutical composition comprising dissolving the isoxazoline compound as above in the solvent and then adsorbing the resulting solution on to the solid carrier excipient.

In one embodiment of this method the solid carrier is microcrystalline cellulose.

In another embodiment of this method the solvent is 2-pyrrolidone or dimethyl acetamide.

Another aspect of the current invention is a method of controlling parasite infestation in an animal comprising administering to the animal a therapeutically effective amount of the composition as described above.

Another aspect of the current invention is a solid oral pharmaceutical composition comprising an isoxazoline compound of Formula (I) or a salt or solvate thereof, and 2-pyrrolidone.

In one embodiment the isoxazoline compound is fluralaner.

In one embodiment the isoxazoline compound is 4-[5-(3,5-dichlorophenyl)-4,5-dihydro-5-(trifluoromethyl)-3-isoxazolyl]-N—[(Z)-(methoxyimino)methyl]-2-methylbenzamide.

In one embodiment the isoxazoline compound is afoxolaner.

In one embodiment the isoxazoline compound is 4-[5-(3,5-dichlorophenyl)-5-(trifluoromethyl)-4H-isoxazol-3-yl]-2-methyl-N-(thietan-3-yl)benzamide.

In one embodiment the isoxazoline compound is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide.

In one embodiment the solid oral pharmaceutical composition is a soft chewable veterinary pharmaceutical composition for oral administration.

Another aspect of the current invention is a method of controlling parasite infestation in an animal comprising administering to the animal a therapeutically effective amount of the composition as described above.

DETAILED DESCRIPTION OF THE INVENTION

Figure 1:
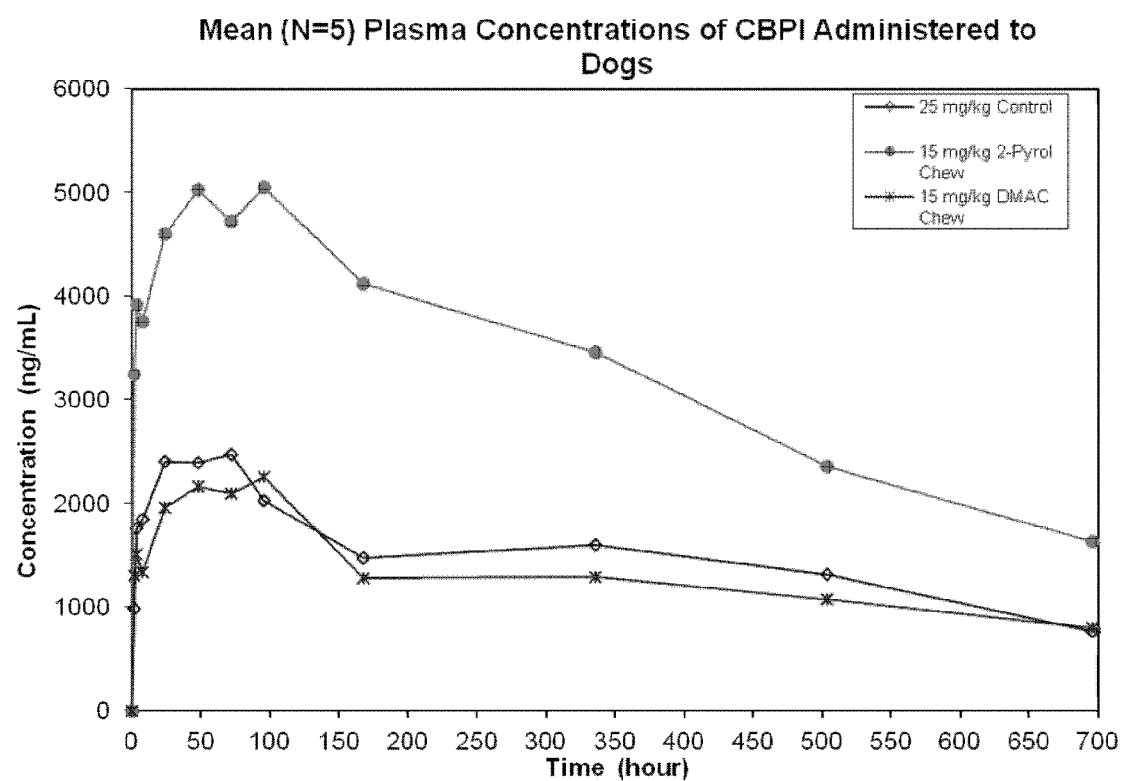
FIG. 1—mean plasma concentration of the CPBI compound fluralaner administered orally to dogs.

The present invention relates to the formulation of a solid oral dosage form (sometimes referred to as solid pharmaceutical composition or formulation) containing an isoxazoline compound of Formula (I) (as described below), that provides significantly improved bioavailability of such isoxazoline compound after administration to an animal.

Specifically, in this formulation the isoxazoline compound of Formula (I) is dissolved in a solvent. This drug solution is then adsorbed onto a solid carrier which is incorporated into a traditional solid oral dosage form. Utilizing pre-dissolved isoxazoline compounds of Formula (I) in the formulation significantly improves the bioavailability of the active drug substance compared to traditional solid oral dosage forms containing the active drug substance incorporated as a solid.

As indicated in the example the inventors discovered, that with dimethylacetamide (DMAC) as solvent for isoxazoline compounds in a solid oral dosage form similar pharmacokinetic profiles were obtained when it was s dosed at a lower dose compared to dosage forms with the active incorporated in higher dosage as a solid.

When 2-pyrrolidone (2-pyrol) was utilized as the solvent in the formulation, significantly higher plasma levels were observed compared to the control, even with the formulation comprising an isoxazoline compound dosed at a lower dose.

This formulation approach provides unexpectedly significant improvement in bioavailability, enabling a significantly lower dosage required to achieve similar or superior pharmacokinetic profiles. Hence, similar blood levels can be achieved that lead to similar effectiveness to control parasites but with a reduced dosage of the isoxazoline compound.

The solid oral dosage form according to the invention comprises an isoxazoline compound of the Formula (I)

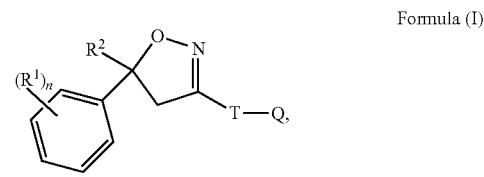

Formula (I)

wherein

R$^1$=halogen, CF$_3$, OCF$_3$, CN, n=integer from 0 to 3, preferably 1, 2 or 3, R$^2$=C$_1$-C$_3$-haloalkyl, preferably CF$_3$ or CF$_2$Cl, T=5- or 6-membered ring, which is optionally substituted by one or more radicals Y, Y=methyl, halomethyl, halogen, CN, NO$_2$, NH$_2$—C═S, or two adjacent radicals Y form together a chain CH—CH═CH—CH, N—CH═CH—CH, CH—N═CH—CH, CH—CH═N—CH, or CH—CH═CH—N, HC═HC—CH, CH—CH═CH, CH═CH—N, N—CH═CH;

Q=X—NR$^3$R$^4$ or a 5-membered N-heteroaryl ring, which is optionally substituted by one or more radicals Z$^A$, Z$^B$ Z$^D$;

X=CH$_2$, CH(CH$_3$), CH(CN), CO, CS,

R$^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

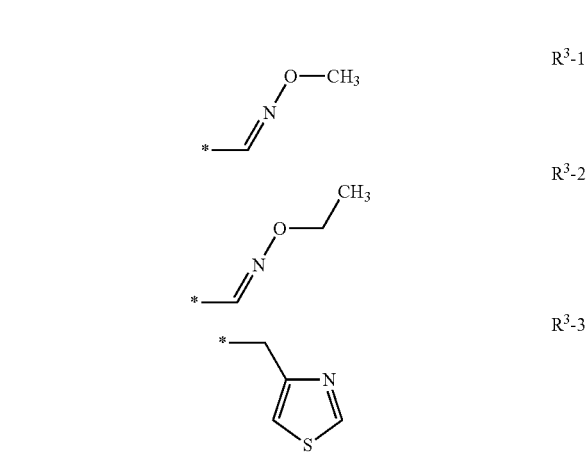

-continued

R³-4 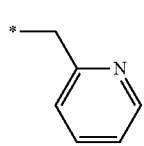

R³-5 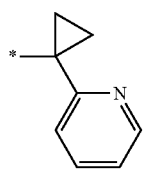

R³-6 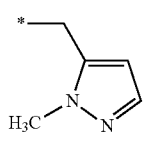

R³-7 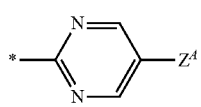

R³-8 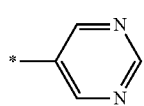

R³-9 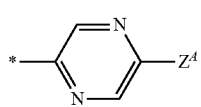

R³-10 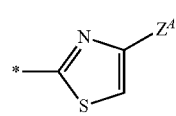

R³-11 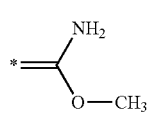

R³-12 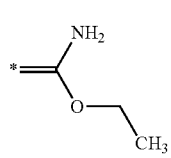

R³-13 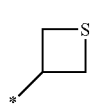

R³-14 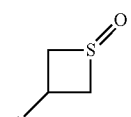

R³-15 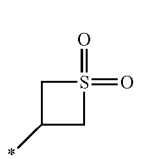

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or $R^3$ and $R^4$ together form a substituent selected from the group consisting of:

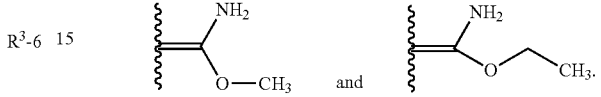

wherein $Z^A$=hydrogen, halogen, cyano, halomethyl ($CF_3$);

or a salt or solvate thereof, a solid carrier and a solvent, wherein the solvent is selected from 2-pyrrolidone, dimethylacetamide or mixtures thereof.

In one preferred embodiment in Formula (I) T is selected from

T-1 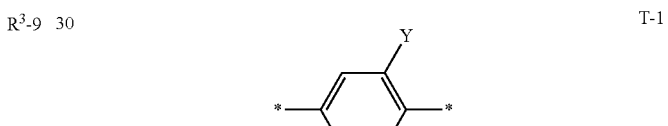

T-2 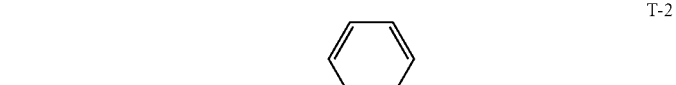

T-3 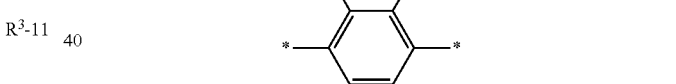

T-4 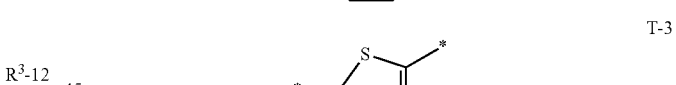

T-5 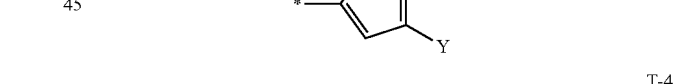

T-6 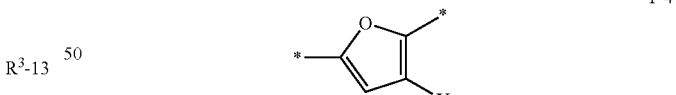

wherein in T-1, T-3 and T-4 the radical Y is hydrogen, halogen, methyl, halomethyl, ethyl, haloethyl.

In an preferred embodiment in Formula (I) Q is selected from

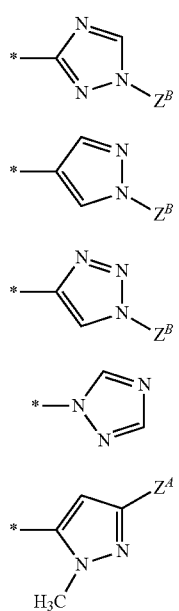
Wherein R³, R⁴, X and Z^A are as defined above.
$Z^B$ =
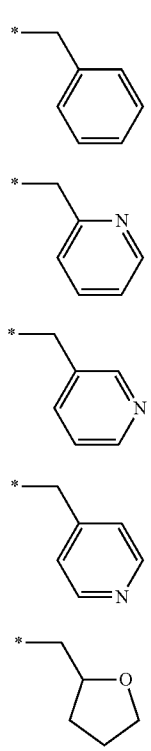
$Z^D$ =
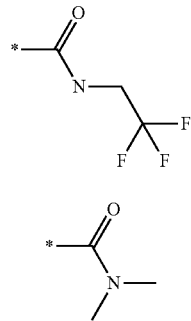
Preferred compounds of Formula (I) are:
| (R¹)ₙ | R² | R³ | R⁴ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |

-continued

| (R¹)ₙ | R² | R³ | R⁴ | T | Y | Q | Z | X |
|---|---|---|---|---|---|---|---|---|
| 3-Cl, 5Cl | CF₃ | CH₂C(O)NHCH₂CF₃ | H | T-2 | — | Q-1 | — | C(O) |
| 3-Cl, 5Cl | CF₃ | CH₂C(O)NHCH₂CH₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-CF₃ | CF₃ | CH₂C(O)NHCH₂CH₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-CF₃, 5-Cl | CF₃ | CH₂C(O)NHCH₂CH₃ | H | T-2 | — | Q-1 | — | C(O) |
| 3-Cl, 5Cl | CF₃ | — | | T-2 | — | Q-6 | $Z^B$-7 | |
| 3-Cl, 5Cl | CF₃ | — | — | T-2 | — | Q-7 | $Z^B$-7 | |
| 3-Cl, 5Cl | CF₃ | — | — | T-2 | — | Q-5 | $Z^B$-7 | |
| 3-Cl, 5Cl | CF₃ | — | — | T-2 | — | Q-2 | $Z^D$-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-Cl, 5Cl | CF₃ | CH₂C(O)NHCH₂CH₃ | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-CF₃, 5-CF₃ | CF₃ | CH₂C(O)NHCH₂CH₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CH₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CH₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-Cl, 5-Cl | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CH₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-CF₃, 5-CF₃ | CF₃ | CH₂C(O)NHCH₂CH₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂C(O)NHCH₂CH₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | CH₂C(O)NHCH₂CH₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

Especially preferred compounds of Formula (I) are

| (R¹)ₙ | R² | R³ | R⁴ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-Cl, 5Cl | CF₃ | — | | T-2 | — | Q-6 | $Z^B$-7 | |
| 3-Cl, 5Cl | CF₃ | — | — | T-2 | — | Q-7 | $Z^B$-7 | |
| 3-Cl, 5Cl | CF₃ | — | — | T-2 | — | Q-5 | $Z^B$-7 | |
| 3-Cl, 5Cl | CF₃ | — | — | T-2 | — | Q-2 | $Z^D$-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |

-continued

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2CH_2SCH_3$ | H | T-21 | — | Q-1 | — | C(O) |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

A more preferred compound has the Formula (II),

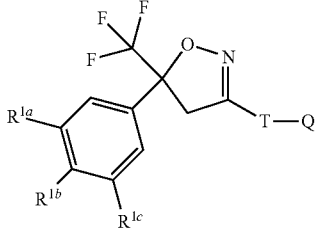

Formula II wherein $R^{1a}$, $R^{1b}$, $R^{1c}$ are independently from each other hydrogen, Cl or $CF_3$, preferably $R^{1a}$ and $R^{1c}$ are Cl or $CF_3$ and $R^{1b}$ is hydrogen, T is

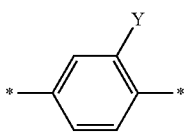
T-1

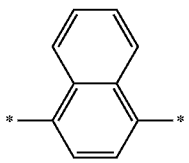
T-2

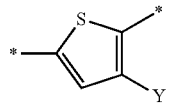
T-3

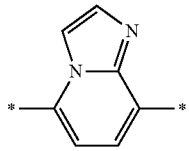
T-20

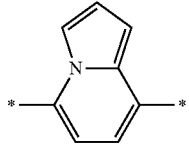
T-21 wherein Y is methyl, bromine, Cl, F, CN or $C(S)NH_2$, and Q is as described above.

In another preferred embodiment in $R^3$ is H and $R^4$ is $-CH_2-C(O)-NH-CH_2-CF_3$, $-CH_2-C(O)-NH-CH_2-CH_3$, $-CH_2-CH_2-CF_3$ or $-CH_2-CF_3$.

In one embodiment the compound of Formula (I) is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3—USAN fluralaner).

In another embodiment the compound of Formula (I) is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the compound of Formula (I) is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In another embodiment the compound of Formula (I) is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN—afoxolaner) that was disclosed in WO2007/079162-.

In another embodiment the compound of Formula (I) is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN 1231754-09-8) that was disclosed in WO2010/070068.

An especially preferred compound is

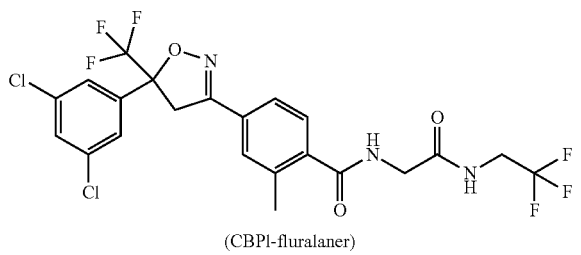 [SMILES: Cc1cc(C2=NOC(c3cc(Cl)cc(Cl)c3)(C(F)(F)F)C2)ccc1C(=O)NCC(=O)NCC(F)(F)F]

(CBPI-fluralaner)

Especially preferred compounds of Formula (II) are:

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | | T-2 | — | Q-5 | $Z^B$-7 | |
| 3-Cl, 5Cl | $CF_3$ | — | | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

Isoxazoline compounds are known in the art and these compounds and their use as parasiticide are described, for example, in US patent application No. US 2007/0066617, and International Patent applications WO 2007/079162, WO 2009/002809, WO 2009/024541, WO 2009/003075, WO2009/080250, WO 2010/070068, WO 2010/079077, WO 2011/075591 and WO 2011/124998, the disclosures of which, as well as the references cited herein, are incorporated by reference. This class of compounds is known to possess excellent activity against ectoparasites such as ticks and fleas.

The isoxazoline compounds may exist in various isomeric forms. A reference to an isoxazoline compound always includes all possible isomeric forms of such compound. Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Isoxazoline compounds of Formula (I) can be prepared according to one or other of the processes described e.g. in Patent Applications US 2007/0066617, WO 2007/079162, WO 2009/002809, WO 2009/080250, WO 2010/070068, WO 2010/079077, 2011/075591 and WO 2011/124998 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

The formulations according to the invention are effective for long durations of time in the treatment of ectoparasites of mammals and, in particular, of fleas and ticks in small mammals such as dogs and cats.

The amount of the isoxazoline compound of Formula (I) in the formulation may be in the range of 1-15% w/w. In an alternative embodiment the amount of such compound may be in the range of 2.0-7.5% w/w. The preferred range is 3.0-4.5% w/w.

In one embodiment, the composition comprises a solid carrier, e.g. microcrystalline cellulose, colloidal silicone dioxide, polyvinyl pyrrolidone or other solid carrier excipient with appropriate characteristic behaviours.

In one embodiment the solid carrier is microcrystalline cellulose (10.0-50.0% w/w, preferred 15.0-25.0% w/w).

In the formulation according to the invention one preferred solvent is a pyrrolidone solvent, especially 2-pyrrolidone. Alternatively other pyrrolidone solvents such as N-methylpyrrolidone can be used.

Another preferred solvent is dimethyl acetamide (DMAC). The preferred range of dimethyl acetamide (DMAC) is 2.0-35.0% w/w. Alternative solvents for use in the current invention dimethyl sulfoxide, dimethyl formamide, diethylene glycol monoethyl ether, ethyl lactate, ethylene monomethyl ether, glycofurol, N,N-diethyl-m-toluamide (DEET) or other solvent with suitable solubility for the compound of Formula (I). Solvent combinations may also be utilized in the formulation according to the invention. The preferred range of such other solvents is 2.0-35.0% w/w.

The amount of the pyrrolidone solvent, especially 2-pyrrolidone in the formulation may be in the range of 2.5-30.0% w/w. The preferred range is 7.0-12.0% w/w. The preferred range of other dimethyl acetamide is 2.0-35.0% w/w.

In one embodiment, the solid oral dosage form is a soft chew. In another embodiment, the solid oral dosage form is a conventional (hard) tablet. Such tablet can include a coating or can include excipients for extended release that are known in the art. In yet another embodiment, granules for oral administration or capsules are employed.

"Soft chew" or "Soft chewable veterinary pharmaceutical product" is intended to mean a product which is solid at room temperature and that is soft to chew and which is functionally chewy because the product has some plastic texture during the process of mastication in the mouth. Such soft chews have a softness that is similar to a cooked ground meat patty.

In soft chew formulations the forming agent is important for the texture of the soft chew and the possibility to form single soft chews from the dough that stay intact and separate. Forming agents are agents providing texture to the soft chew product, like for example polyethylene glycol (PEG), microcrystalline wax, cetyl alcohol or polyvinylpyrrolidone (PVP). In an embodiment, the forming agent is polyethylene glycol (PEG). Moreover, depending upon the desired consistency of the soft chew, different molecular weight PEG may be utilized. In an embodiment, PEG 8000 is utilized. However, the PEG chosen is a matter of choice and the molecular weight may be higher or lower than 8000, but preferably higher than 600. Alternatively PEG 3500 might be used.

In an embodiment, the forming agent comprises about 3.0% to about 35% w/w of the pharmaceutical composition. In an alternate embodiment, a forming agent comprises about 4.5% to about 30% w/w % of the pharmaceutical composition. In an alternate embodiment, a forming agent comprises about 10% to about 20% w/w of the pharmaceutical composition. In case the forming agent is polyvinylpyrrolidone e.g. 2, 4, 5, 6 or 9% w/w are present in the soft chew.

A preferred formulation for the solid oral pharmaceutical composition includes:
4.4% w/w compound of Formula (I), especially fluralaner
10.5% w/w 2-pyrrolidone
25.0% w/w microcrystalline cellulose
5.1% w/w sodium starch glycolate
15.0% w/w flavour
2.0% w/w sodium lauryl sulphate
2.5% w/w sodium pamoate
0.5% w/w aspartame
0.5% w/w magnesium stearate
1.5% w/w glycerol
17.25% w/w soybean oil
15.75% w/w PEG8000

The amount of glycerol in the formulation may range from 0-12.0% with the preferred range of 0.5-10.0%. Soybean oil amounts may range from 5.0-25.0% with the preferred range of 10.0-22.0%. Desired ranges of the other excipients include sodium starch glycolate (2.0-15.0%), flavor (5-25%), sodium lauryl sulfate (0.05-5.0%), sodium pamoate (0.01-5.0%), aspartame (0.01-2.0%), and magnesium stearate (0.01-2.0%).

The formulation according to the current invention conventionally further comprise physiologically acceptable formulation excipients known in the art e.g. as described in "Gennaro, Remington: The Science and Practice of Pharmacy" (20th Edition, 2000) incorporated by reference herein. All such ingredients, carriers and excipients must be substantially pharmaceutically or veterinary pure and non-toxic in the amounts employed and must be compatible with the pharmaceutically active ingredients.

Additional excipients that can be present in the formulation are e.g. one or more fillers, one or more flavours, or sugar components, surfactants, stabilizers, flow agents, disintegration agents, preservatives and/or lubricating agents.

This invention is also directed to formulations as described above with combinations comprising more than one pharmaceutically active ingredient, e.g. in addition to the compound of Formula (I) another compound of Formula (I) or a pharmaceutically active ingredient with a different structure.

Preferred combinations comprising active ingredients selected from the group consisting of isoxazoline compounds of Formula (I) or (II) and avermectins and milbemycins. In one embodiment the formulation, especially soft chew comprises a combination of an isoxazoline compound of Formula (I), especially fluralaner or afoxolaner, with ivermectin. In another embodiment the soft chew comprises a combination of an isoxazoline compound of Formula (I), especially fluralaner por afoxolaner, with milbemycin or with moxidectin.

Other combinations of the present invention can include insect or acarid growth regulators (AGRs or IGRs) such as e.g. fenoxycarb, lufenuron, diflubenzuron, novaluron, triflumuron, fluazuron, cyromazine, methoprene, pyriproxyfen etc., thereby providing both initial and sustained control of parasites (at all stages of insect development, including eggs) on the animal subject, as well as within the environment of the animal subject.

The inventors discovered that oral solid dosage forms of isoxazoline compounds of Formula (I) as described above, especially of fluralaner, afoxoloaner can be produced that result in a higher bioavailability of the isoxazoline compound after administration to animals. In such methods the isoxazoline compound of Formula (I) is first dissolved in a suitable solvent (e.g. 2-pyrol or DMAC) and then adhered to a solid carrier (e.g. microcrystalline cellulose). Such process can be used in general for various solid oral dosage forms such as hard tablets, granules, capsules or soft chews (soft chewable tablets).

A general method for preparing a solid oral dosage form, such as a soft chewable tablet formulation comprises the steps of:
1. Dissolve the isoxazoline compound (e.g. fluralaner or afoxolaner) in the solvent (e.g. 2-pyrrolidone) to form a solution.
2. Add the isoxazoline solution to the solid carrier (e.g. microcrystalline cellulose) and mix to form a first dry mixture.
3. Add all other dry excipients to the first dry mixture and mix to form a second dry mixture.
4. Add liquid ingredients, glycerol and soybean oil, to the second dry mixture. Mix to form wet mass.
5. Melt a wax (e.g. polyethylene glycol 8000) and add to the wet mass. Mix well to form the final bulk mass.
6. Form appropriately sized chewable tablets In an embodiment the tablets may be formed from the final bulk mass utilizing a forming machine. Alternatively, the tablets may be formed by other means known in the art. For example, the tablets may be formed by hand.

Methods of Using the Solid Oral Pharmaceutical Compositions

In one embodiment the product of the invention is intended for use for controlling a parasitic insect-, acarid and/or helminth, especially parasitic insect and/or acarid infestation. The term "controlling a parasitic insect- and/or acarid infestation" refers to preventing, reducing or eliminating an infestation by such parasites on animals preferably by killing the insects and/or acarids or nematode parasites within hours or days.

The term "parasitic insect- and acarid" refers to ectoparasites e.g. insect and acarine pests that commonly infest or infect animals. Examples of such ectoparasites include the egg, larval, pupal, nymphal and adult stages of lice, fleas, mosquitoes, mites, ticks, and biting or nuisance fly species. Especially important are fleas and ticks, especially their adult stages.

Examples of invertebrate parasitic pests controlled by administering the solid oral formulation of this invention to an animal to be protected include ectoparasites (arthropods, acarines, etc) and endoparasites (helminths, e.g., nematodes, trematodes, cestodes, acanthocephalans, etc.).

In particular, the formulations of this invention are effective against ectoparasites including: flies such as *Haematobia* (*Lyperosia*) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis*, *Hypoderma lineatum*, *Lucilia sericata*, *Lucilia cuprina* (green blowfly), *Calliphora* spp. (blowfly), *Protophormia* spp., *Oestrus ovis* (nasal botfly), *Culicoides* spp. (midges), *Hippobosca equine*, *Gastrophilus instestinalis*, *Gastrophilus haemorrhoidalis* and *Gastrophilus naslis*; lice such as *Bovicola* (*Damalinia*) *bovis*, *Bovicola equi*, *Haematopinus asini*, *Felicola subrostratus*, *Heterodoxus spiniger*, *Lignonathus setosus* and *Trichodectes canis*; keds such as *Melophagus ovinus*; mites such as *Psoroptes* spp., *Sarcoptes scabei*, *Chorioptes bovis*, *Demodex equi*, *Cheyletiella* spp., *Notoedres cati*, *Trombicula* spp. and *Otodectes cyanotis* (ear mites); ticks such as *Ixodes* spp., *Boophilus* spp., *Rhipicephalus* spp., *Amblyomma* spp., *Dermacentor* spp., *Hyalomma* spp. and *Haemaphysalis* spp.; and fleas such as *Ctenocephalides felis* (cat flea) and *Ctenocephalides canis* (dog flea).

In general, the formulations according to the invention will contain an effective amount of the isoxazoline compounds of Formula (I) as defined above, meaning a non-toxic but sufficient amount to provide the desired control effect. A person skilled in the art using routine experimentation may determine an appropriate "effective" amount in any individual case. Such an amount will depend on the age, condition, weight and type of the target animal.

The solid oral dosage forms may be formulated to contain an amount of the isoxazoline compound of Formula (I) that is adjusted to animals in a specific weight range. The animals may receive a dosage of the solid oral formulation according to the invention every 2, 3, 4, 5 or 6 months or receives a monthly, weekly or daily dosage. The treatment can, for example, be continuing or seasonal. The time period between treatments depends upon factors such as the parasite(s) being treated, the degree of infestation, the type of mammal or bird and the environment where it resides. It is well within the skill level of the practitioner to determine a specific administration period for a particular situation.

The solid oral formulations of the present invention are especially suitable for combating parasites that infest mammals (including humans). Mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Of particular note is the embodiment wherein the animals to be protected are domesticated dogs (i.e. *Canis lupus familiaris*) and domestic house cats (i.e. *Felis catus*).

In some embodiments of this invention, the solid oral formulation of an isoxazoline of Formula (I) is administered to treat parasitoses of an animal (or make a medicament to treat parasitoses of an animal). The term "parasitoses" includes pathologic conditions and diseases associated with or caused by one or more ectoparasites directly, such as, for example, anemia and flea allergy dermatitis. It also includes pathologic conditions or diseases associated with caused by one or more vector-transmitted pathogens, such as, for example, Lyme disease, Ehrlichiosis (particularly Canine Ehrlichiosis), and Rocky Mountain spotted fever from vector ticks.

This invention also relates to treatment methods wherein at least an ancillary goal of controlling ectoparasites in and/or on an animal is to control an ectoparasitic infestation in an environment that is occupied (periodically or continuously) by the animal. In some such embodiments, for example, the animal is a companion animal (e.g., a cat or dog). The environment may be, for example, a house or other shelter; a room; a pen, a stall, or other confinement means; bedding; etc.

This invention also is directed to kits that are, for example, suitable for use in performing the treatment methods described above. In general, such a kit will comprise an oral solid formulation according to the invention comprising a therapeutically effective amount of a isoxazoline of Formula (I), and an additional component(s). The additional component(s) may be, for example, one or more of the following: a diagnostic tool, instructions for administering the composition, an apparatus for administering the composition, a container comprising an excipient or other active ingredient to be mixed or administered in combination with the composition, or a memory aid (e.g., a stamp to adhere to a calendar to remind an animal owner of a time to administer a subsequent dose of the composition).

As used herein, the term "w/w" designates weight/weight, the term "w/v" designates weight/volume, and the term "mg/kg" designates milligrams per kilogram of body weight. As used herein, % w/w represents the percentage by weight of an ingredient in the recipe of the product.

The invention having been fully described, its practice is illustrated by the examples provided below. The examples do not limit the scope of the invention, which is defined entirely by the appended claims.

EXAMPLES

Example 1

An embodiment for a direct compression tablet containing two active ingredients includes:
0.015% w/w ivermectin
2.5% w/w fluralaner
0.1% w/w citric acid
0.5% w/w Cremaphor RH40
4.5% w/w 2-pyrrolidone
50.0% w/w microcrystalline cellulose
33.735% w/w corn starch
8.0% w/w flavor
0.5% magnesium stearate
0.1% w/w aspartame
0.05% w/w red iron oxide Example 2

An embodiment for soft chewable tablets containing two active ingredients includes:
0.42% w/w moxidectin
1.67% w/w fluralaner
0.2% w/w citric acid
4.0% w/w 2-pyrol
10.0% w/w microcrystalline cellulose
3.0% w/w flavor 0.2% w/w aspartame
4.0% w/w Klucel
30.51% w/w soy grits
4.0% w/w propylene glycol
4.0% w/w Miglyol 812
8.0% w/w cetyl alcohol
10.0% w/w Cremaphor RH40
20.0% w/w sodium starch glycolate Example 3

Additional embodiments for the soft chewable tablets include:
5.333% w/w fluralaner
9.0% w/w 2-pyrrolidone
11.0% w/w microcrystalline cellulose
5.0% w/w Pluronic 127
5.0% w/w sodium lauryl sulfate
10.0% w/w flavor
5.0% w/w sodium starch glycolate
16.667% soy grits
2.0% w/w Labrasol
13.0% w/w Labrafac PG
18.0% w/w PEG3350

Example 4

7.25% w/w fluralaner
10.5% w/w 2-pyrrolidone
22.75% microcrystalline cellulose
2.0% colloidal silicone dioxide
3.5% w/w Lutrol Micro 127
3.5% w/w sodium lauryl sulfate
15.0% w/w flavor
0.5% w/w aspartame
0.5% w/w magnesium stearate
2.0% w/w Labrasol
14.75% w/w soybean oil
15.25% w/w PEG8000

Example 5

7.5% w/w fluralaner
7.0% w/w dimethyl acetamide
23.5% microcrystalline cellulose
15.0% w/w flavor
7.5% w/w sodium starch glycolate
3.5% w/w sodium lauryl sulfate
2.0% w/w sodium pamoate
0.5% w/w magnesium stearate
0.5% w/w aspartame
7.0% w/w glycerol
10.0% w/w soybean oil
16.0% w/w PEG8000

Example 6

4.4% w/w fluralaner
10.5% w/w 2-pyrrolidone
25.0% microcrystalline cellulose
15.0% w/w flavor
5.1% w/w sodium starch glycolate
3.5% w/w sodium lauryl sulfate
2.5% w/w sodium pamoate
0.5% w/w magnesium stearate
0.5% w/w aspartame
3.0% w/w glycerol 14.25% w/w soybean oil
15.75% w/w PEG8000

Example 7

Multiple formulations were evaluated for their impact on bioavailability of Fluralaner when formulated in a soft chewable tablet.

The descriptions of selected formulations are listed below.

TABLE 1

| Excipient | Control Formulation | 2-Pyrol Formulation | DMAC Formulation |
|---|---|---|---|
| fluralaner | 13.64% | 4.4% | 7.5% |
| 2-pyrrollidone | | 10.5% | |
| dimethylacetamide | | | 7.0% |
| Avicel PH102 | | 25.0% | 23.5% |
| flavor | 20.0% | 15.0% | 15.0% |
| corn starch | 16.06% | | |
| sodium starch glycolate | | 5.1% | 7.5% |
| sucrose | 7.0% | | |
| sodium lauryl sulfate | 2.0% | 3.5% | 3.5% |
| sodium pamoate | 2.0% | 2.5% | 2.0% |
| magnesium stearate | 0.75% | 0.5% | 0.5% |
| aspartame | 0.25% | 0.5% | 0.5% |
| glycerol | 7.5% | 3.0% | 7.0% |
| soybean oil | 12.3% | 14.25% | 10.0% |
| Polyethylene Glycol 3350 | 18.5% | | |
| Polyethylene Glycol 8000 | | 15.75% | 16.0% |

Dimethylacetamide (DMAC) is a good solvent for the active (A-1443) with a solubility of 791.5 mg/mL. However, when utilized in this type of formulation approach, similar pharmacokinetic profiles were obtained compared to chewable tablets with the active incorporated as a solid (control). Given that the DMAC formulation was dosed at a lower dose (15 mg/kg compared to 25 mg/kg for the control), these results are improvements in dose adjusted pharmacokinetic measurements (Cmax and AUC) over the control (see Table 2 and FIG. 1).

When 2-pyrrolidone (2-pyrol) was utilized as the solvent in the formulation (solubility 775.41 mg/mL), significantly higher plasma levels were observed compared to the control, even with the formulation dosed at a lower dose (15 mg/kg compared to 25 mg/kg for the control). Dose normalized pharmacokinetic measurements (Cmax and AUC) for the 2-pyrol formulation are more than double that of the DMAC formulation and more than triple that of the control (see Table 2 and FIG. 1). These results were unexpected.

This formulation approach provides significant improvement in bioavailability, enabling a significantly lower dosage required to achieve similar to superior pharmacokinetic profiles.

TABLE 2

| Pharmacokinetic Parameter | Control Formulation | 2-Pyrol Formulation | DMAC Formulation |
|---|---|---|---|
| $T_{1/2}$ (days) | 20.3 | 21.6 | 21.3 |
| Tmax (hours) | 40.8 | 55.2 | 48.8 |
| Cmax (ng/mL) | 2832 | 5973 | 2511 |
| Dose (mg/kg) | 25 | 15 | 15 |
| Cmax/Dose (kg * ng/mL/mg) | 113 | 398 | 167 |

TABLE 2-continued

| Pharmacokinetic Parameter | Control Formulation | 2-Pyrol Formulation | DMAC Formulation |
|---|---|---|---|
| $AUC_{0\text{-}inf}$ (h * ng/mL) | 1501420 | 3562496 | 1531455 |
| $AUC_{0\text{-}inf}$/Dose (h * kg * ng/mL/mg) | 60057 | 237500 | 102097 |
| Bioavailability | 27.8% | 109.8% | 47.2% |

Example 8

Pharmacokinetic Profile Following Oral Administration of Chewable Formulations of Isoxazoline Compounds The objective of this study is to compare the blood plasma pharmacokinetic profile of three different isoxazoline compounds in two different chewable formulations after a single oral (PO) administration of in dogs.

Test Formulations:

The following compounds were formulated according to the invention. Specifically, the isoxazoline compound was first dissolved in a solvent, i.e. 2-pyrrolidone. This drug solution was then adsorbed onto the solid carrier, i.e. microcrystalline cellulose, which was incorporated into a solid oral dosage form as described in the specification with excipients as described in Table 3. Comparative example formulation ID No. 13-009, 13-011 and 13-013 contain the active drug substance incorporated as a solid that was manufactured as described in general in the specification without prior pre-dissolving the active ingredient and adsorption to the solid carrier.

(Isoxazoline) Compound A

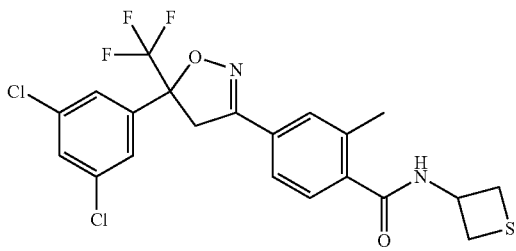

(Isoxazoline) Compound B

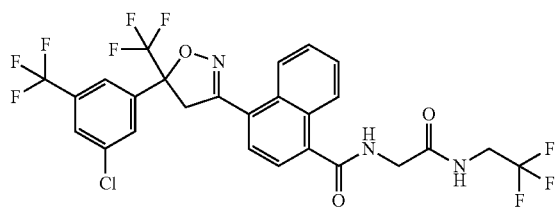

(Isoxazoline) Compound C

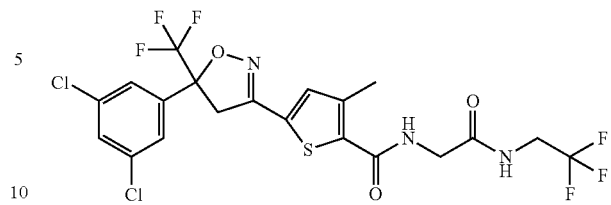

TABLE 3

Test formulations

| Excipient | 13-009 | 13-010 | 13-011 | 13-012 | 13-013 | 13-014 |
|---|---|---|---|---|---|---|
| Compound A | 13.64% | 4.27% | | | | |
| Compound B | | | 13.64% | 4.27% | | |
| Compound C | | | | | 13.64% | 4.27% |
| 2-pyrrolidone | | 10.19% | | 10.19% | | 10.19% |
| microcrystalline cellulose | | 24.27% | | 24.27% | | 24.27% |
| sodium starch glycolate | | 4.95% | | 4.95% | | 4.95% |
| flavor | 20.0% | 14.56% | 20.0% | 14.56% | 20.0% | 14.56% |
| sucrose | 7.0% | | 7.0% | | 7.0% | |
| corn starch | 16.06% | | 16.06% | | 16.06% | |
| sodium lauryl sulfate | 2.0% | 3.4% | 2.0% | 3.4% | 2.0% | 3.4% |
| sodium pamoate | 2.0% | 2.43% | 2.0% | 2.43% | 2.0% | 2.43% |
| magnesium stearate | 0.75% | 0.49% | 0.75% | 0.49% | 0.75% | 0.49% |
| aspartame | 0.25% | 0.49% | 0.25% | 0.49% | 0.25% | 0.49% |
| glycerin | 7.5% | 2.91% | 7.5% | 2.91% | 7.5% | 2.91% |
| soybean oil | 12.3% | 16.75% | 12.3% | 16.75% | 12.3% | 16.75% |
| PEG 3350 | 18.5% | | 18.5% | | 18.5% | |
| PEG 8000 | | 15.29% | | 15.29% | | 15.29% |

Study Design

The test compounds were administered orally to four beagle dogs per dose group for a total of twenty-four dogs.

Experimental Design: Randomized Complete Block Design

TABLE 4

Study Design

| Treatment ID | No. of dogs | Formulation ID | Compound ID | Dose (mg/kg) | Formulation Type[2,3] |
|---|---|---|---|---|---|
| 1 | 4 | 13-009 | A | 25 | Control Chew |
| 2 | 4 | 13-010 | A | 10 | Alternate Chew |
| 3 | 4 | 13-011 | B | 25 | Control Chew |
| 4 | 4 | 13-012 | B | 10 | Alternate Chew |
| 5 | 4 | 13-013 | C | 25 | Control Chew |
| 6 | 4 | 13-014 | C | 10 | Alternate Chew |

[2]Control Chew-compound is not dissolved when formulated into chew (comparative example).
[3]Alternate Chew-compound is dissolved when formulated into chew Each animal was administered the tablet or chew by placing it in the back of the oral cavity over the tongue to initiate swallowing.

Plasma was obtained from the collected blood samples and analyzed for concentrations of the test compounds. Individual blood samples (approximately 4.5 mL per sample) were taken via jugular venipuncture into sodium-citrate tubes from all dogs for drug analysis. Blood samples were collected at the following time points: pretreatment (within 2 h prior to dosing) and approximately 1, 2, 4, 6, 8, 24, 48, 72 hours after dosing (±15 min). A final blood sample was taken from each dog on Day 7 (±2 h after the time of dosing on Day 0).

Figure 2:
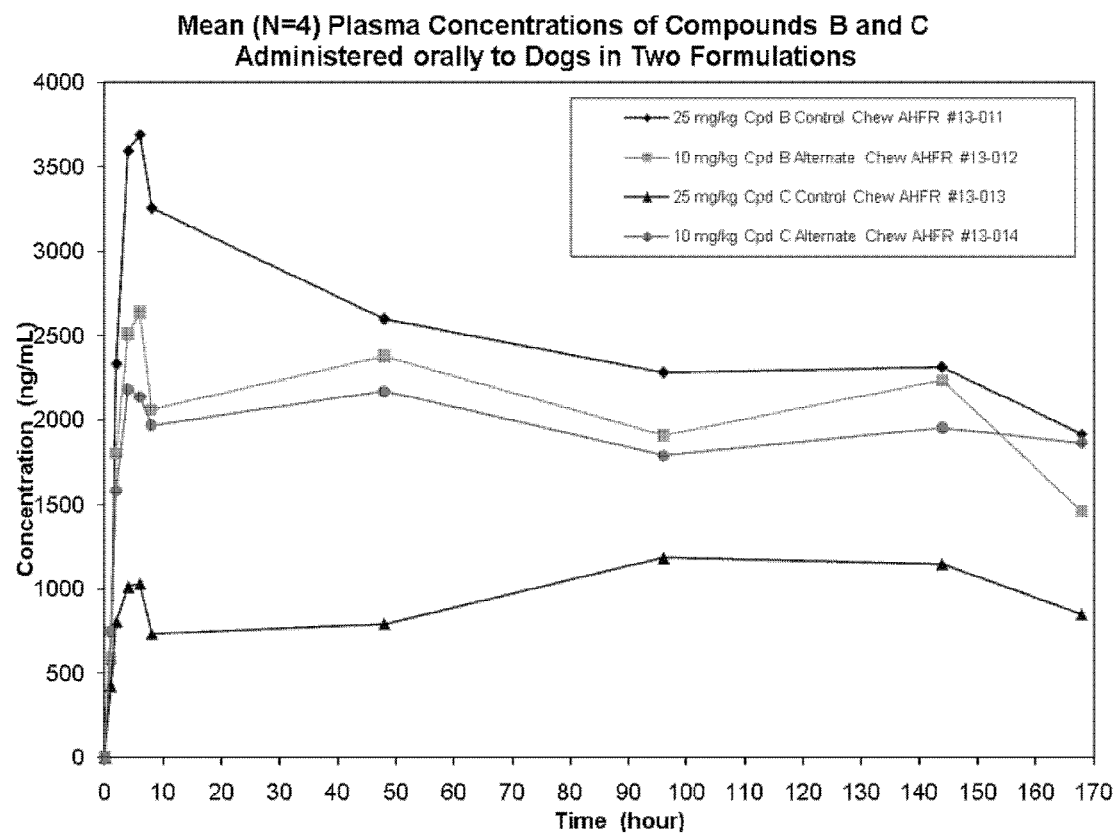
FIG. 2—mean plasma concentration of the isoxazoline compounds afoxolaner and -[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide administered orally to dogs.

Results:

When 2-pyrrolidone (2-pyrol) was utilized as the solvent in the formulation (alternate chew), similar or even higher plasma levels were observed compared to the control chew, even with the formulation dosed at a lower dose (10 mg/kg compared to 25 mg/kg for the control)—see FIG. 2.

Pharmacokinetic analysis was performed on the plasma concentration data with the computer program Pharsight WinNonlin Enterprise, Version 4.0.1, or more recent update (Model 200: plasma data, extravascular input).

Dose normalized pharmacokinetic measurements (Cmax and AUC) for the 2-pyrol formulation (alternate chew) are much higher, in some cases more than double to five times that of the control formulation (see Table 5).

This formulation approach provides significant improvement in the bioavailability relative to the control formulation, enabling a significantly lower dosage required to achieve similar to superior pharmacokinetic profiles. These results were unexpected.

TABLE 5

| Pharmacokinetic Parameter | Control Compound A | Dissolved Compound A | Control Compound B | Dissolved Compound B | Control Compound C | Dissolved Compound C |
|---|---|---|---|---|---|---|
| Dose (mg/kg) | 25 | 10 | 25 | 10 | 25 | 10 |
| Tmax (h) | | | 5.0 | 15.5 | 27.5 | 15.5 |
| Cmax (ng/mL) | 19.2 | 17.1 | 4340 | 3213 | 1589 | 2538 |
| Cmax/Dose (kg*ng/mL/mg) | 0.768 | 1.71 | 174 | 321 | 63.5 | 254 |
| $AUC_{(0-168h)}$ (h*ng/mL) | ND | ND | 416522 | 334163 | 164332 | 326601 |
| $AUC_{(0-168h)}$/Dose (h*kg*ng/mL/mg) | ND | ND | 16661 | 33416 | 6573 | 32660 |

Example 9

Efficacy Against Brown Dog Ticks (R. sanguineus) on Dogs

A solid pharmaceutical composition according to the invention with the following excipients was prepared.

| Excipient | Composition (% w/w) |
|---|---|
| Fluralaner | 4.27% |
| 2-pyrrolidone | 10.19% |
| microcrystalline cellulose | 24.27% |
| sodium starch glycolate | 4.95% |
| flavor | 14.56% |
| sodium lauryl sulfate | 3.40% |
| sodium pamoate | 2.43% |
| aspartame | 0.49% |
| magnesium stearate | 0.49% |
| glycerol | 2.91% |
| soybean oil | 16.75% |
| Polyethylene Glycol 8000 | 15.29% |

Dogs were randomly assigned to 4 treatment groups of 8 animals each, and one untreated control group of 8 animals. The dogs in the treatment groups were treated with the composition as described above on Day Zero as shown in Table 6:

TABLE 6

| | Treatment Groups | |
|---|---|---|
| Group | Treatment | |
| A | Untreated control | |
| B | 4.27% fluralaner chewable tablet | 8 mg/kg bw |
| C | 4.27% fluralaner chewable tablet | 10 mg/kg bw |
| D | 4.27% fluralaner chewable tablet | 12 mg/kg bw |
| E | 4.27% fluralaner chewable tablet | 20 mg/kg bw |

The dogs were infested on Day −2 with approximately 50 adult unfed ticks (R. sanguineus) and on Day 28 and 56. Ticks were counted approximately 48 h post infestation and on Days 30 and 58 (approximately 48 hour after each post-treatment re-infestation) to evaluate the acaricidal activity in the treated groups.

Table 7 Shows the Observed Tick Counts:

TABLE 7

| Brown Dog Ticks (R. sanguineus) on dogs- Tick counts - | | | |
|---|---|---|---|
| Group | Day 2 | Day 30 | Day 58 |
| A | 21.25 | 23 | 25.9 |
| B | 0 | 0 | 0 |
| C | 0.125 | 0 | 0 |
| D | 0 | 0 | 1.13 |
| E | 0 | 0 | 0 |

What is claimed is:

1. A soft chewable veterinary pharmaceutical composition for oral administration comprising an isoxazoline compound of Formula (I)

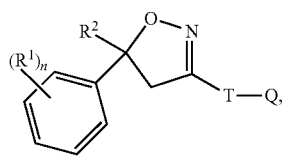

Formula (I)

wherein
$R^1$=halogen, $CF_3$, $OCF_3$, CN,
n=integer from 0 to 3, $R^2$=$C_1$-$C_3$-haloalkyl, T=5- or 6-membered ring, which is optionally substituted by one or more radicals Y, Y=methyl, halomethyl, halogen, CN, $NO_2$, $NH_2$—C=S, or two adjacent radicals Y form together a chain;

Q=X—$NR^3R^4$ or a 5-membered N-heteroaryl ring, which is optionally substituted by one or more radicals;

X=$CH_2$, CH($CH_3$), CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

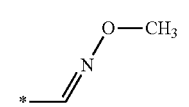
R³-1

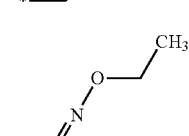
R³-2

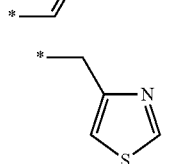
R³-3

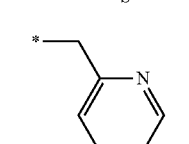
R³-4

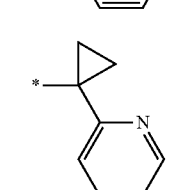
R³-5

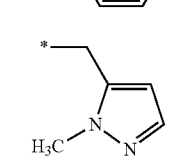
R³-6

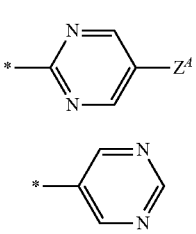
R³-7

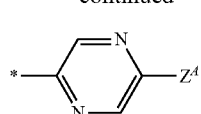
R³-8

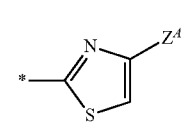
R³-9

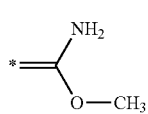
R³-10

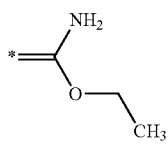
R³-11

R³-12

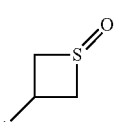
R³-13

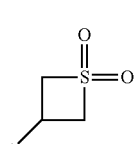
R³-14

R³-15 wherein $Z^A$=hydrogen, halogen, cyano, halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

Or $R^3$ and $R^4$ together form a substituent selected from the group consisting of:

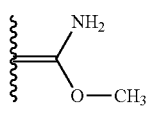 and 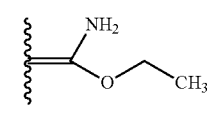

or a salt or solvate thereof, a solid carrier and a solvent wherein the solvent is selected from 2-pyrrolidone, dimethyl acetamide or mixtures thereof; and wherein the isoxazoline compound is dissolved in the solvent and then the resulting solution is adsorbed on to the solid carrier.

2. The soft chewable veterinary pharmaceutical composition of claim 1 wherein the solid carrier is microcrystalline cellulose.

3. The soft chewable veterinary pharmaceutical composition of claim 1 wherein the solvent is 2-pyrrolidone.

4. The soft chewable veterinary pharmaceutical composition of claim 1 wherein the solvent is dimethyl acetamide.

5. The soft chewable veterinary pharmaceutical composition of claim 1 wherein the isoxazoline compound is fluralaner.

6. The soft chewable veterinary pharmaceutical composition of claim 1 wherein the isoxazoline compound is 4-[5-(3,5-dichlorophenyl)-4,5-dihydro-5-(trifluoromethyl)-3-isoxazolyl]-N—[(Z)-(methoxyimino)methyl]-2-methyl-benzamide.

7. The soft chewable veterinary pharmaceutical composition of claim 1 wherein the isoxazoline compound is afoxolaner.

8. The soft chewable veterinary pharmaceutical composition of claim 1 wherein the isoxazoline compound is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide.

9. The soft chewable veterinary pharmaceutical composition of claim 1 wherein the isoxazoline compound is 4-[5-(3,5-dichlorophenyl)-5-(trifluoromethyl)-4H-isoxazol-3-yl]-2-methyl-N-(thietan-3-yl)benzamide.

10. The soft chewable veterinary pharmaceutical composition of claim 1 wherein the composition comprises an additional pharmaceutically active compound.

11. The soft chewable veterinary pharmaceutical composition of claim 6 comprising an additional pharmaceutically active compound wherein the additional pharmaceutically active compound is a macrocyclic lactone selected from the group of ivermectin, milbemycin, and moxidectin.

12. The soft chewable veterinary pharmaceutical composition according to claim 1 wherein the composition comprises an isoxazoline compound of Formula (I) or a salt or solvate thereof, 2-pyrrolidone, Microcrystalline cellulose, Sodium starch glycolate, Sodium lauryl sulfate, Sodium Pamoate, Magnesium Stearate, Aspartame, Glycerol, Soybean Oil, and Polyethylene Glycol.

13. The soft chewable veterinary pharmaceutical composition according to claim 1 wherein the composition comprises an isoxazoline compound of Formula (I) or a salt or solvate thereof, dimethyl acetamide, Microcrystalline cellulose, Sodium starch glycolate, Sodium lauryl sulfate, Sodium Pamoate, Magnesium Stearate, Aspartame, Glycerol, Soybean Oil, and Polyethylene Glycol.

14. A method of controlling parasite infestation in an animal comprising administering to the animal a therapeutically effective amount of the composition of claim 1.

15. The method of claim 14 wherein the isoxazoline compound is fluralaner.

16. The soft chewable veterinary pharmaceutical composition of claim 1, wherein n is 1, 2 or 3.

17. The soft chewable veterinary pharmaceutical composition of claim 1, wherein $R^2$ is $CF_3$ or $CF_2Cl$.

18. The soft chewable veterinary pharmaceutical composition of claim 1, wherein two adjacent radicals Y form together a three or four membered chain.

* * * * *